United States Patent
Zhang et al.

(10) Patent No.: US 10,299,846 B2
(45) Date of Patent: May 28, 2019

(54) AUTOMATIC WIRE-DIRECTING INTRAMEDULLARY REDUCTION DEVICE USED FOR LONG BONE FRACTURE

(71) Applicant: Yingze Zhang, Shijiazhuang, Hebei Province (CN)

(72) Inventors: Yingze Zhang, Shijiazhuang (CN); Wei Chen, Shijiazhuang (CN); Juan Wang, Shijiazhuang (CN)

(73) Assignee: Yingze Zhang, Shijiazhuang, Hebei (CN)

( * ) Notice: Subject to any disclaimer, the term of this patent is extended or adjusted under 35 U.S.C. 154(b) by 838 days.

(21) Appl. No.: 14/894,763

(22) PCT Filed: Feb. 25, 2015

(86) PCT No.: PCT/CN2015/073268
§ 371 (c)(1),
(2) Date: Nov. 30, 2015

(87) PCT Pub. No.: WO2015/139550
PCT Pub. Date: Sep. 24, 2015

(65) Prior Publication Data
US 2016/0106491 A1    Apr. 21, 2016

(30) Foreign Application Priority Data
Mar. 20, 2014  (CN) .......................... 2014 1 0104782

(51) Int. Cl.
*A61B 17/92* (2006.01)
*A61B 17/72* (2006.01)
*A61B 17/88* (2006.01)

(52) U.S. Cl.
CPC ............ *A61B 17/921* (2013.01); *A61B 17/72* (2013.01); *A61B 17/8872* (2013.01)

(58) Field of Classification Search
CPC . A61B 17/88; A61B 17/8869; A61B 17/8872; A61B 17/8897
(Continued)

(56) References Cited

U.S. PATENT DOCUMENTS 4,050,528 A * 9/1977 Foltz .................. A61B 17/1628
173/170
4,091,880 A * 5/1978 Troutner ............ A61B 17/1628
173/170
(Continued)

FOREIGN PATENT DOCUMENTS

CN   1863487 A    11/2006
CN   102448389 A   5/2012
(Continued)

OTHER PUBLICATIONS

International Search Report for International Application No. PCT/CN2015/073268, dated May 28, 2015, with English translation.
The CN1OA issued by CNIPA dated Jun. 26, 2014.

*Primary Examiner* — Eric S Gibson
(74) *Attorney, Agent, or Firm* — Yunling Ren

(57) ABSTRACT

Provided is an automatic wire-directing intramedullary reduction device used for long bone fracture including a holder, a reduction bushing mounted at the holder; a reduction head rotatably mounted at the reduction bushing; a pipe for guide wire mounted at the holder, a reduction rod received in the reduction bushing with the front end of the reduction rod connecting to the other side at the rear end of the reduction head, the reduction rod will drive the reduction head to rotate around a shaft when moving back and forth, a fixing handle fixed at the rear part of the holder; a wire-directing handle rotatably connected to the fixing handle, a pushing plate for guide wire disposed between the front part and the rear part of the holder, a guide wire passing through the pipe for guide wire, a return spring for pushing
(Continued)

plate sleeved around the guide wire, the wire-directing handle will drive the pushing plate for guide wire and the guide wire to move forward when rotating around the rotate shaft.

20 Claims, 2 Drawing Sheets

(58) Field of Classification Search
USPC .............................................. 606/96–98, 104
See application file for complete search history.

(56) References Cited

U.S. PATENT DOCUMENTS

| | | | |
|---|---|---|---|
| 5,002,543 A | 3/1991 | Bradshaw et al. | |
| 5,496,327 A * | 3/1996 | Den Ouden | A61B 17/92 606/103 |
| 5,718,707 A | 2/1998 | Mikhail | |
| 5,728,128 A * | 3/1998 | Crickenberger | A61F 2/4657 606/102 |
| 5,800,437 A * | 9/1998 | Gustilo | A61B 17/885 606/79 |
| 5,902,306 A * | 5/1999 | Norman | A61B 17/1697 606/104 |
| 5,911,722 A * | 6/1999 | Adler | A61B 17/1624 174/170 |
| 6,030,387 A * | 2/2000 | Ballier | A61B 17/62 606/104 |
| 6,264,661 B1 * | 7/2001 | Jerger | A61B 17/1697 606/100 |
| 6,319,258 B1 * | 11/2001 | McAllen, III | A61B 17/068 227/175.1 |
| 6,599,295 B1 * | 7/2003 | Tornier | A61B 17/0401 606/104 |
| 7,326,203 B2 * | 2/2008 | Papineau | A61B 17/32002 606/104 |
| 7,922,724 B2 * | 4/2011 | Lim | A61B 17/7086 606/104 |
| 8,221,433 B2 * | 7/2012 | Lozier | A61B 17/068 606/104 |
| 8,308,701 B2 * | 11/2012 | Horvath | A61F 9/0008 604/294 |
| 8,609,003 B2 | 12/2013 | Vaidya | |
| 8,690,889 B2 * | 4/2014 | Colesanti | A61B 17/064 606/104 |
| 9,333,019 B2 * | 5/2016 | Khosla | A61B 17/8861 |
| 9,687,257 B2 * | 6/2017 | Straslicka | A61B 17/8897 |
| 2002/0188301 A1 * | 12/2002 | Dallara | A61B 17/064 606/104 |
| 2005/0119667 A1 * | 6/2005 | Leport | A61B 17/7091 606/104 |
| 2007/0088362 A1 * | 4/2007 | Bonutti | A61B 17/0218 606/99 |
| 2011/0071578 A1 * | 3/2011 | Colesanti | A61B 17/064 606/305 |
| 2012/0253411 A1 * | 10/2012 | Lozier | A61B 17/068 606/329 |
| 2013/0085504 A1 * | 4/2013 | Bryant | A61B 17/8869 606/103 |
| 2014/0074105 A1 * | 3/2014 | Peultier | A61B 17/7083 606/104 |
| 2016/0106491 A1 * | 4/2016 | Zhang | A61B 17/921 606/96 |

FOREIGN PATENT DOCUMENTS

| | | |
|---|---|---|
| CN | 103610489 A | 3/2014 |
| CN | 103815957 A | 5/2014 |
| CN | 203749549 U | 8/2014 |
| DE | 19751731 A1 | 5/1999 |
| WO | 2011067668 A1 | 6/2011 |

* cited by examiner

AUTOMATIC WIRE-DIRECTING INTRAMEDULLARY REDUCTION DEVICE USED FOR LONG BONE FRACTURE

CROSS REFERENCE TO RELATED PATENT APPLICATIONS

This application is an US national phase of International Application No. PCT/CN2015/073268, filed Feb. 25, 2015, which is based upon and claims priority to Chinese Patent Application No. 201410104782.3, filed on Mar. 20, 2014, and the entire content thereof is incorporated herein by reference.

TECHNICAL FIELD

The present disclosure relates to a field of medical apparatus, particularly, relates to an automatic wire-directing intramedullary reduction device used for long bone fracture.

BACKGROUND

In orthopedic clinical treatments, long bone fracture is a kind of common damage. Operation solution for long bone fracture mainly includes two kinds of method, i.e. open reduction and internal fixation, and closed reduction and internal fixation.

In the operation solution of open reduction and internal fixation, the fracture part is reduced in sight and fixed by reconstruction plate or intramedullary nail. The above method has advantageous of high quality of reduction. However, the above method has defects as follows: open operation is required, which results in large wound and massive bleeding of patient, moreover, during operation, hematomas around fracture part which contains factor aiding in the healing of fracture are removed, thus being not good for the healing of fracture. Furthermore, skin and the tissue are incised, and muscle and other tissues around fracture part are separated, therefore incidence of complications such as infection is high.

As for the operation solution of the closed reduction and internal fixation, it has advantageous of small wound and less bleeding of patient, and hematomas around fracture part which contains factor aiding in the healing of fracture are retained, therefore complications such as infection and non-union of fracture have a relative lower incidence. However, the above method has defects as follows: it needs high technical requirement of reduction and fixing for doctors. It is difficult to reach reduction, especially for comminuted fracture or serious lateral displacement, takes long time for operation, and needs high dose reagent for X-ray fluoroscopy.

Currently, with the development of medical technology, microinvasive operation is widely used in various kinds of operations, which provides new method for improving operation quality, speeding the process of recovery and reducing suffering of patient. Consequently, there is a tendency to adopt the method of closed reduction for treating long bone fracture. However, in current operations of closed reduction, it is difficult to perform reduction for fracture with lateral displacement since no special device could be used, thus affecting the accuracy of reduction and operation quality, which becomes an unsolved problem in the treatment for long bone fracture up to now.

Furthermore, after performing reduction, a guide wire should be directed into the medullary cavity of fracture segment at the opposite side, and then the accessory of intramedullary nail is used to perform reduction and fixing for fracture part. However, the guide wire is directed by hand with large amount of blood attached on apparatus and gloves, which results in skid, the guide wire is directed with low speed, and the length thereof is unstable and difficult to be controlled. Therefore, how to improve the method of directing the guide wire is a problem that should be solved quickly.

The foresaid information as disclosed in the background part only serves to enhance understanding of the background of the present disclosure, thereby it may not contain ordinary skill information that has been well known.

SUMMARY

In view of the above, the present disclosure is intended to provide an automatic wire-directing intramedullary reduction device used for long bone fracture, by way of which a minimally-invasive reduction for long bone fracture having lateral displacement and rotation displacement can be completed rapidly, and the improvements to the accuracy of reduction and the quality of operation is accordingly achieved. As a result of the automatic wire-directing, the defects of low speed and unstable length and so on, caused by manual wire-directing, can be avoided.

Additional aspects and advantages of the present disclosure will be in part set forth in the description below, and in part will become obvious from the description, or may be learned from the practice of present disclosure.

In one aspect, the present disclosure provides an automatic wire-directing intramedullary reduction device used for long bone fracture comprising a holder having a front part, a rear part and a middle part connecting to a side of the front part and the rear part; a reduction bushing mounted at the front part of the holder; a reduction head, one side at the rear end of the reduction head is rotatably mounted at a front end of the reduction bushing; a pipe for guide wire mounted at the front part of the holder and parallel with the reduction bushing; a reduction rod received in the reduction bushing with the front end of the reduction rod connecting to the other side at the rear end of the reduction head, the reduction rod will drive the reduction head to rotate around a shaft when moving back and forth; a fixing handle fixed at the rear part of the holder; a wire-directing handle, an upper part of the wire-directing handle rotatably connected to the fixing handle by a rotate shaft; a pushing plate for guide wire disposed between the front part and the rear part of the holder, and provided with a wire-directing hole corresponding to the position of the pipe for guide wire; a guide wire passing through the pipe for guide wire via the wire-directing hole of the pushing plate for guide wire, a return spring for pushing plate sleeved around the guide wire which is between the pushing plate for guide wire and the front part of the holder, an upper part of the wire-directing handle is behind the pushing plate for guide wire, and the wire-directing handle will drive the pushing plate for guide wire and the guide wire to move forward when rotating around the rotate shaft.

In an embodiment of the present disclosure, the pushing plate for guide wire is perpendicular to an axis of the pipe for guide wire.

In an embodiment of the present disclosure, it further comprises a seat of reduction head mounted at a front end of the reduction bushing, and one side at the rear end of the reduction head is rotatably mounted at the seat of reduction head.

In an embodiment of the present disclosure, a lower side at the rear end of the reduction head is connected to a side wall of the seat of reduction head by a horizontal rotate shaft, and an upper side at the rear end of the reduction head is connected to the front end of the reduction rod by a rotate shaft.

In an embodiment of the present disclosure, it further comprises a driving and transmission mechanism to move the reduction rod back and forth.

In an embodiment of the present disclosure, the driving and transmission mechanism comprises a gear box disposed at the front part of the holder, both of the reduction rod and pipe for guide wire are mounted in the gear box, the guide wire is configured to pass through the gear box from the front end to the rear end thereof, and the reduction rod, which has a rack, is configured to pass in and out of the gear box at its rear part; a gear disposed in the gear box and engaged with the rack at the rear part of the reduction rod; and a knob provided outside the gear box and having the same rotate shaft as the gear so as to rotate the gear.

In an embodiment of the present disclosure, it further comprises a hook rotatably mounted outside the gear box by a rotate shaft and having hooking parts at both sides of the rotate shaft and a spanner; and a compression spring connecting to the spanner and contacting the knob, and the hooking part of the hook tightly presses against the rack of the reduction rod through the elasticity of the compression spring.

In an embodiment of the present disclosure, it further comprises a baffle plate rotatably connecting to the rear part of the holder at an upper end of the baffle plate; and holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

In an embodiment of the present disclosure, a diameter of the wire-directing hole of the pushing plate for guide wire matches a diameter of the guide wire, and a diameter of guide wire hole of the baffle plate matches a diameter of the guide wire.

The present disclosure brings about positive effects as follow: in the present disclosure, the reduction bushing may be planted into the medullary cavity of one end of the fractured long bones, the reduction head is cocked up by pulling the reduction rod in the reduction bushing, then the front end of the reduction head may be inserted into the medullary cavity of fracture segment at the opposite side through the fracture part; and the reduction head becomes straight by pushing the reduction rod in the reverse direction, so as to poke the medullary cavity at the opposite side, thus realizing the reduction for the fracture part at the opposite side. After finishing the reduction, the guide wire is directed into the medullary cavity at the opposite side by the wire-directing mechanism, and the fracture part is reduced and fixed using the accessory of intramedullary nail. The present disclosure could perform reduction for the fracture part with lateral displacement, or with lateral displacement and rotation, therefore, it could rectify lateral displacement and rotation displacement simultaneously. The present disclosure could perform wire feeding automatically by the mechanized wire-directing device, thus allowing for rapid, convenient, stable, and easy-to-control wire feeding, which avoids defects of low speed and unstable length and so on caused by manual wire feeding. The present disclosure is simple in structure, facilitated to use, and could rapidly complete reduction with minimally invasive for long bone fracture having lateral displacement and rotation displacement, improve the accuracy of reduction and operation quality, and solve the unsolved problems for a long time. Consequently, the present disclosure is an effectively device for treating long bone fracture through the method of closed reduction.

The above and other features and advantages of the present disclosure will become more apparent from the detailed description of exemplary embodiments thereof with reference to accompany drawings.

Figure 1:
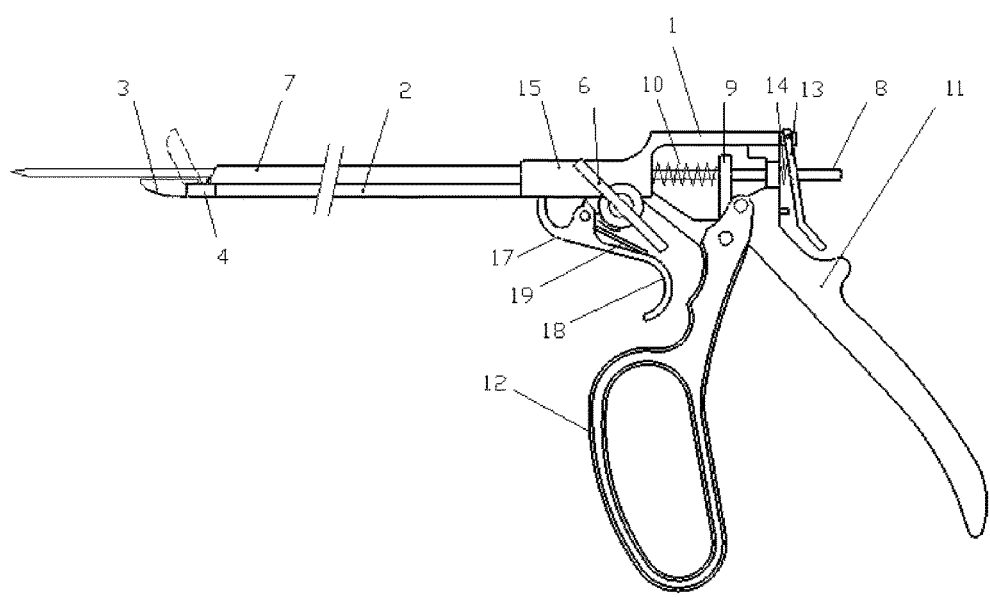
FIG. 1 is a schematic view of the automatic wire-directing intramedullary reduction device used for long bone fracture according to an embodiment of the present disclosure.

Reference numerals in the above drawings are as follows: holder 1, reduction bushing 2, reduction head 3, seat of reduction head 4, reduction rod 5, handle 6, pipe for guide wire 7, guide wire 8, pushing plate for guide wire 9, return spring for pushing plate 10, fixing handle 11, wire-directing handle 12, baffle plate 13, spring for baffle plate 14, gear box 15, knob 16, hook 17, spanner 18, and compression spring 19.

DETAILED DESCRIPTION

Specific embodiments in this disclosure have been shown by examples in the foregoing drawings and are hereinafter described in detail. The figures and written description are not intended to limit the scope of the inventive concepts in any manner. Rather, they are provided to illustrate the inventive concepts to a person skilled in the art by reference to particular embodiments. The same or similar features employing identical reference numerals, and the detailed description thereof is omitted.

Figure 2:
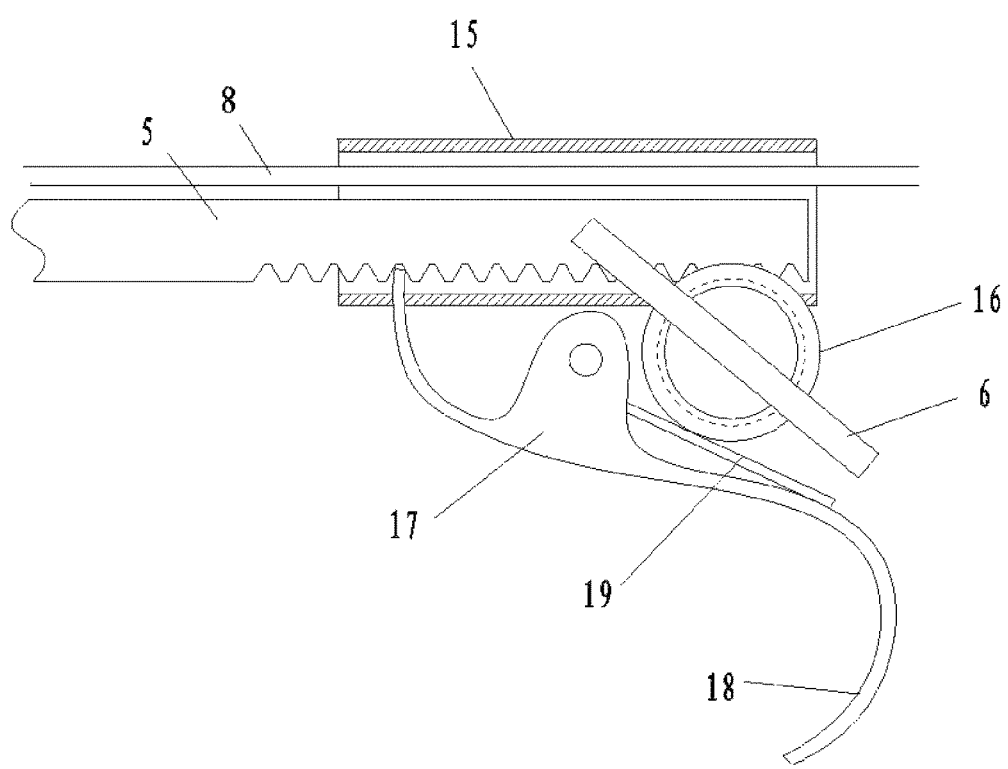
FIG. 2 is a driving and transmission mechanism of the automatic wire-directing intramedullary reduction device used for long bone fracture according to an embodiment of the present disclosure.

As shown in FIGS. 1 and 2, the automatic wire-directing intramedullary reduction device used for long bone fracture according to the present disclosure includes a holder 1, a fixing handle 11, a reduction mechanism and a wire-directing mechanism. Rear part of the fixing handle 11 and the rear part of the holder 1 are connected together.

The holder 1 may be an integral structure with a front part, a rear part and a middle part connecting to the side of the front part and rear part. The middle part may be formed by one or more connecting ribs.

The reduction mechanism includes a reduction bushing 2, a reduction head 3, a seat of reduction head 4 and a driving and transmission mechanism.

The rear end of the reduction bushing 2 connects to the front end of the holder 1. One side at the rear end of the reduction head 3 is rotatably mounted in the seat of reduction head 4 by a rotate shaft. The seat of reduction head 4 is fixed to a front end of the reduction bushing 2. The reduction rod 5 is received in the reduction bushing 2 with the front end of the reduction rod 5 connecting to the other side at the rear end of the reduction head 3. In detail, a lower side at the rear end of the reduction head 3 connects to a side wall of the seat of reduction head 4 by a horizontal rotate shaft, and an upper side at the rear end of the reduction head 3 connects to the front end of the reduction rod 5 by a rotate shaft. The reduction head 3 may be directly disposed at the front end of the reduction bushing 2 in a case that no seat of reduction head 4 is provided.

As shown in FIG. 2, in the present embodiment, the driving and transmission mechanism used for moving the reduction rod 5 back and forth includes a gear box 15, a gear, and a knob 16.

The gear box 15 may be fixed at the front part of the holder 1. Under the said condition, both of the reduction rod 5 and pipe for guide wire 7 are mounted in the gear box 15. The guide wire 8 passes through the gear box 15 from the front end to the rear end. The reduction rod 5 having rack passes through the gear box 15 at the rear part. The gear is mounted in the gear box 15 and engaged with the rack at the rear part of the reduction rod 5. The knob 16 is provided at external of the gear box 15 which facilitates to screw. The gear has the same rotate shaft as the knob 16 so as to be rotated with the driving by the knob 16. In order to conveniently rotate the knob 16, a handle 6 may be provided on the knob 16, which has a length larger than the diameter of the knob 16, such that the knob 16 may be rotated more easily.

The structure of the driving and transmission mechanism is not limited thereto, any other structure capable of moving the reduction rod 5 back and forth is adaptable for the present disclosure.

During operation, the knob 16 is rotated clockwise so as to rotate the gear having the same rotate shaft as the knob 16 simultaneously, the reduction rod 5 is pulled backward as the rack thereof is pulled by the gear, then the reduction head 3 is pulled to rotate around a rotate shaft connecting to the seat of reduction head 4 at the lower part of the reduction head 3 by the reduction rod 5, such that the front end of the reduction head 3 is cocked up and inserted into the medullary cavity of fracture segment at the opposite side through the fracture part, and then the knob 16 is rotated anticlockwise, such that the gear pushes forward the reduction rod 5, therefore, the reduction head 3 rotates anticlockwise around the rotate shaft. During anticlockwise rotation of the reduction head 3, the reduction head 3 will gradually become straight, the reduction for fracture segment at the opposite side may be completed by virtue of the poking force of the reduction head 3 and the force applied to the medullary cavity at the opposite side by the main body of the reduction device.

Concerning the fracture having lateral displacement and rotation displacement, the following steps may be operated so as to complete the reduction and rectify lateral displacement and rotation displacement simultaneously based on the above process: fixing the reduction head 3 at an appropriate angle, and then rotating the entire reduction device.

As shown in FIGS. 1 and 2, in order to automatically lock the reduction head 3 at the cocking or straight position, a hook 17 is provided under the lower part of the gear box 15. In detail, the hook 17 is rotatably mounted outside the gear box 15 by a rotate shaft, which has hooking parts at both sides of the rotate shaft and a spanner 18 on which a compression spring 19 is provided. The hooking part at the front end of the hook 17 may insert into the gear box 15 via a hole on the gear box 15 and embed into the rack of the reduction rod 5. The compression spring 19 contacts the knob 16, and the hooking part of the hook 17 may tightly press against the rack of the reduction rod 5 through the elasticity of the compression spring 19.

Generally, the hooking part at the front end of the hook 17 embeds into the rack through a rotate shaft by the compression spring 19, such that the rack is locked and can not move back and forth. When the knob 16 is rotated no matter clockwise or anticlockwise, the gear generates pushing trend for the movement of the rack. In case that the pushing force produced by the rotation of the knob 16 is larger than the compression force applied by the compression spring 19 to the rack, the front end of the hook 17 may be pushed outward by the rack, thus unlocking the rack, and the reduction rod 5 may move back and forth. Once the knob 16 stop rotating, the front end of the hook 17 may re-embedded into the rack through rotate shaft by the compression spring 19, such that the rack is locked automatically and can not move back and forth.

As shown in FIG. 1, the wire-directing portion includes a pipe for guide wire 7, a guide wire 8, a pushing plate for guide wire 9, a return spring for pushing plate 10 and a wire-directing handle 12.

The pipe for guide wire 7 connects to the upper side of the reduction bushing 2 with the rear end of the pipe for guide wire 7 connecting to the front end of the holder 1. The pipe for guide wire 7 is parallel with the reduction bushing 2. The pushing plate for guide wire 9 is located at the back of the pipe for guide wire 7, which may be perpendicular to the axis of the pipe for guide wire 7. The pushing plate for guide wire 9 is provided with a wire-directing hole, through which the guide wire 8 is directed into the pipe for guide wire 7.

As shown in FIG. 1, the upper part of the wire-directing handle 12 is rotatably connected to the fixing handle 11 by a rotate shaft. The end of the wire-directing handle 12 above the rotate shaft is behind the pushing plate for guide wire 9. The return spring for pushing plate 10 is located between the pushing plate for guide wire 9 and the pipe for guide wire 7. During directing the guide wire, the wire-directing handle 12 is cocked backwards at the lower part so that the wire-directing handle 12 rotates around the rotate shaft, meanwhile, the pushing plate for guide wire 9 is pushed to move forward by the end of the wire-directing handle 12, such that the wire-directing hole of the pushing plate for guide wire 9 upwards presses against the guide wire 8. The guide wire 8 is pushed to move forwards by the friction generated by the forward movement of the pushing plate for guide wire 9, thereby completing the wire feeding.

After finishing one process of wire feeding via the wire-directing handle 12, the wire-directing handle 12 is loosed, such that the return spring for pushing plate 10 pushes the pushing plate for guide wire 9 and the wire-directing handle 12 back to the initial position. During the backward movement of the pushing plate for guide wire 9, the pushing plate for guide wire 9 does not compress the guide wire 8, such that the guide wire 8 can not move backwards without the friction generated by the pushing plate for guide wire 9. Therefore, the guide wire 8 may be moved to the next process of wire feeding until reaching a required length.

In an embodiment of the present disclosure, the distance of one process of wire feeding by the wire-directing handle 12 is 5 mm. The required length may be reached by cocking the wire-directing handle 12 several times by the operator based on requirement on site.

As shown in FIG. 1, in an embodiment, the present disclosure is further provided with a baffle plate 13 and a spring for baffle plate 14. The upper end of the baffle plate 13 rotatably connects to the rear part of the holder 1. Both the rear part of the holder 1 and the baffle plate 13 have holes of guide wire correspondingly with each other. The spring for baffle plate 14 is disposed between the baffle plate 13 and the holder 1. The guide wire 8 passes through the holes of guide wire in the baffle plate 13 and the holder 1 from rear to front, and then reaches the wire-directing hole of the pushing plate for guide wire 9. Normally, the guide wire hole of the baffle plate 13 tightly presses against the guide wire 8 upwards. Before inserted, the guide wire 8 could pass through the guide wire hole when the baffle plate 13 is cocked downwards.

If the guide wire 8 is need to be drawn, firstly unlocking the hook 17 so as to leave the reduction head 3 at a flat position, and then pressing downwards the baffle plate 13, finally drawing backwards the guide wire 8.

In the present disclosure, after inserting the guide wire 8 into the fracture segment at the opposite side, drawing the reduction device out of the medullary cavity, and perform fixing and reduction for the fracture part by using the accessory of intramedullary nail.

INDUSTRIAL APPLICABILITY

In the present disclosure, the reduction bushing may be planted into the medullary cavity of one end of the fractured long bones, the reduction head is cocked up by pulling the reduction rod in the reduction bushing, then the front end of the reduction head may be inserted into the medullary cavity of fracture segment at the opposite side through the fracture part; and the reduction head becomes straight by pushing the reduction rod in the reverse direction, so as to pock the medullary cavity at the opposite side, thus realizing the reduction for the fracture part at the opposite side. After finishing the reduction, the guide wire is directed into the medullary cavity at the opposite side by the wire-directing mechanism, and the fracture part is fixed and reduced by using the accessory of intramedullary nail. The present disclosure may perform reduction for the fracture part with lateral displacement, or with lateral displacement and rotation, therefore, it may rectify lateral displacement and rotation displacement simultaneously. The present disclosure could perform wire feeding automatically by the mechanized wire-directing device, thus allowing for rapid, convenient, stable, and easy-to-control wire directing, which avoids defects of low speed and unstable length and so on caused by hand during wire feeding. The present disclosure is simple in structure, facilitated to use, and may rapidly complete reduction with minimally invasive for long bone fracture having lateral displacement and rotation displacement, improve the accuracy of reduction and operation quality, and solve the unsolved problems for a long time. Consequently, the present disclosure is an effectively device for treating long bone fracture during the method of closed reduction.

Exemplary embodiments have been specifically shown and described as above. It is to be understood that both the foregoing general description are exemplary and explanatory only and are not restrictive of the invention. It will be appreciated the aforesaid embodiments may be modified and portions of the technical features therein may be equally changed, which does not depart from the spirit or principle. All suitable modifications and equivalent which come within the spirit and scope of the appended claims are intended to fall within the scope of the present disclosure.

What is claimed is:

1. An automatic wire-directing intramedullary reduction device used for long bone fracture, comprising:
   a holder having a front part, a rear part and a middle part connecting to a side of the front part and the rear part;
   a reduction bushing mounted at the front part of the holder;
   a reduction head, one side at a rear end of the reduction head is rotatably mounted at a front end of the reduction bushing;
   a pipe for guide wire mounted at the front part of the holder and parallel with the reduction bushing;
   a reduction rod received in the reduction bushing with a front end of the reduction rod connecting to the rear end of the reduction head, the reduction rod will drive the reduction head to rotate around a shaft when moving back and forth;
   a fixing handle fixed at the rear part of the holder;
   a wire-directing handle, an upper part of the wire-directing handle rotatably connected to the fixing handle by a rotate shaft;
   a pushing plate for guide wire disposed between the front part and the rear part of the holder, and provided with a wire-directing hole corresponding to a position of the pipe for guide wire;
   a guide wire passing through the pipe for guide wire via the wire-directing hole of the pushing plate for guide wire, a return spring for pushing plate sleeved around the guide wire which is between the pushing plate for guide wire and the front part of the holder, an upper part of the wire-directing handle is behind the pushing plate for guide wire, and the wire-directing handle will drive the pushing plate for guide wire and the guide wire to move forward when rotating around the rotate shaft.

2. The automatic wire-directing intramedullary reduction device used for long bone fracture according to claim 1, wherein, the pushing plate for guide wire is perpendicular to an axis of the pipe for guide wire.

3. The automatic wire-directing intramedullary reduction device used for long bone fracture according to claim 2, further comprising:
   a baffle plate rotatably connecting to the rear part of the holder at an upper end of the baffle plate;
   holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

4. The automatic wire-directing intramedullary reduction device used for long bone fracture according to claim 3, wherein: a diameter of the wire-directing hole of the pushing plate for guide wire is bigger than a diameter of the guide wire, and a diameter of guide wire hole of the baffle plate is bigger than a diameter of the guide wire, during direct the guide wire, the guide wire contacts with pushing plate, so that the guide wire is pushed to move forwards by a friction generated between the guide wire and the pushing plate.

5. The automatic wire-directing intramedullary reduction device used for long bone fracture according to claim 1, further comprising:
   a seat of reduction head mounted at a front end of the reduction bushing, and one side at the rear end of the reduction head is rotatably mounted at the seat of reduction head.

6. The automatic wire-directing intramedullary reduction device used for long bone fracture according to claim 5, wherein, a lower side at the rear end of the reduction head is connected to a side wall of the seat of reduction head by a horizontal rotate shaft, and an upper side at the rear end of the reduction head is connected to the front end of the reduction rod by a rotate shaft.

7. The automatic wire-directing intramedullary reduction device used for long bone fracture according to claim 6, further comprising:
- a baffle plate rotatably connecting to the rear part of the holder at an upper end of the baffle plate;
- holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

8. The automatic wire-directing intramedullary reduction device used for long bone fracture according to claim 7, wherein: a diameter of the wire-directing hole of the pushing plate for guide wire is bigger than a diameter of the guide wire, and a diameter of guide wire hole of the baffle plate is bigger than a diameter of the guide wire, during direct the guide wire, the guide wire contact with the pushing plate, so that the guide wire is pushed to move forwards by a friction generated between the guide wire and the pushing plate.

9. The automatic wire-directing intramedullary reduction device used for long bone fracture according to claim 5, further comprising:
- a baffle plate rotatably connecting to the rear part of the holder at an upper end of the baffle plate;
- holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

10. The automatic wire-directing intramedullary reduction device used for long bone fracture according to claim 9, wherein: wherein: a diameter of the wire-directing hole of the pushing plate for guide wire is bigger than a diameter of the guide wire, and a diameter of guide wire hole of the baffle plate is bigger than a diameter of the guide wire, during direct the guide wire, the guide wire contacts with the pushing plate, so that the guide wire is pushed to move forwards by a friction generated between the guide wire and the pushing plate.

11. The automatic wire-directing intramedullary reduction device used for long bone fracture according to claim 1, further comprising a driving and transmission mechanism to move the reduction rod back and forth.

12. The automatic wire-directing intramedullary reduction device used for long bone fracture according claim 11, wherein, the driving and transmission mechanism comprises:
- a gear box disposed at the front part of the holder, both of the reduction rod and pipe for guide wire are mounted in the gear box, the guide wire is configured to pass through the gear box from the front end to the rear end thereof, and the reduction rod, which has a rack, is configured to pass in and out of the gear box at its rear part;
- a gear disposed in the gear box and engaged with a rack at a rear part of the reduction rod; and
- a knob provided outside the gear box and configured to rotate the gear.

13. The automatic wire-directing intramedullary reduction device used for long bone fracture according to claim 12, further comprising:
- a hook rotatably mounted outside the gear box by a rotate shaft and having hooking parts and a spanner; and
- a compression spring connecting to the spanner and contacting the knob, and the hooking part of the hook tightly presses against the rack of the reduction rod through an elasticity of the compression spring.

14. The automatic wire-directing intramedullary reduction device used for long bone fracture according to claim 13, further comprising:
- a baffle plate rotatably connecting to the rear part of the holder at an upper end of the baffle plate;
- holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

15. The automatic wire-directing intramedullary reduction device used for long bone fracture according to claim 12, further comprising:
- a baffle plate rotatably connecting to the rear part of the holder at an upper end of the baffle plate;
- holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

16. The automatic wire-directing intramedullary reduction device used for long bone fracture according to claim 15, wherein: a diameter of the wire-directing hole of the pushing plate for guide wire is bigger than a diameter of the guide wire, and a diameter of guide wire hole of the baffle plate is bigger than a diameter of the guide wire, during direct the guide wire, the guide wire contacts with the pushing plate, so that the pushed to move forwards by a friction generated between the guide wire and the pushing plate.

17. The automatic wire-directing intramedullary reduction device used for long bone fracture according to claim 11, further comprising:
- a baffle plate rotatably connecting to the rear part of the holder at an upper end of the baffle plate;
- holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

18. The automatic wire-directing intramedullary reduction device used for long bone fracture according to claim 17, wherein: a diameter of the wire-directing hole of the pushing plate for guide wire is bigger than a diameter of the guide wire, and a diameter of guide wire hole of the baffle plate is bigger than a diameter of the guide wire, during direct the guide wire, the guide wire contacts with the pushing plate, so that the pushed to move forwards by a friction generated between the guide wire and the pushing plate.

19. The automatic wire-directing intramedullary reduction device used for long bone fracture according to claim 1, further comprising:
- a baffle plate rotatably connecting to the rear part of the holder at an upper end of the baffle plate;
- holes of guide wire are respectively provided at the rear part of the holder and the baffle plate corresponding to the pipe for guide wire for allowing the guide wire to pass through, and a spring for baffle plate is disposed on the guide wire between the baffle plate and the rear part of the holder.

20. The automatic wire-directing intramedullary reduction device used for long bone fracture according to claim 19, wherein: a diameter of the wire-directing hole of the pushing plate for guide wire is bigger than a diameter of the guide wire, and a diameter of guide wire hole of the baffle plate is bigger than a diameter of the guide wire, during direct the guide wire, the guide wire contacts with the pushing plate, so that the guide wire is pushed to move forwards by a friction generated between the guide wire and the pushing plate.

\* \* \* \* \*